(12) United States Patent
Cooper et al.

(10) Patent No.: US 11,284,902 B2
(45) Date of Patent: Mar. 29, 2022

(54) METHOD OF MAKING A VASCULAR OCCLUSION DEVICE

(71) Applicant: BOSTON SCIENTIFIC SCIMED, INC., Maple Grove, MN (US)

(72) Inventors: Kelsey Rae Cooper, Blaine, MN (US); Reggie Roth, Monticello, MN (US); Liam Ryan, County Waterford (IE); Robert Hannon, Tipperary (IE); James Michael English, Tipperary (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 282 days.

(21) Appl. No.: 16/264,941

(22) Filed: Feb. 1, 2019

(65) Prior Publication Data
US 2019/0231361 A1    Aug. 1, 2019

Related U.S. Application Data
(60) Provisional application No. 62/625,035, filed on Feb. 1, 2018.

(51) Int. Cl.
    *A61B 17/12* (2006.01)
    *B33Y 80/00* (2015.01)
    (Continued)

(52) U.S. Cl.
    CPC .. *A61B 17/12172* (2013.01); *A61B 17/12109* (2013.01); *B33Y 80/00* (2014.12);
    (Continued)

(58) Field of Classification Search
    CPC .......... B22F 10/00; B22F 10/20; B22F 10/10; B22F 2999/00; B22F 5/106; B22F 5/08;
    (Continued)

(56) References Cited

U.S. PATENT DOCUMENTS

| 5,117,839 A | 6/1992 | Dance |
| 5,234,437 A | 8/1993 | Sepetka |

(Continued)

FOREIGN PATENT DOCUMENTS

| EP | 2777542 A2 | 9/2014 |
| EP | 2777545 A2 | 9/2014 |

(Continued)

OTHER PUBLICATIONS

International Search Report and Written Opinion dated Jun. 15, 2018 for International Application No. PCT/US2018/021978.

(Continued)

*Primary Examiner* — Richard G Louis
(74) *Attorney, Agent, or Firm* — Seager, Tufte & Wickhem LLP (57) ABSTRACT

A method of making a vascular occlusion device may include cutting a tubular member to form an expandable frame including a first hub integrally formed with the expandable frame adjacent a first end of the expandable frame, and a plurality of longitudinally-oriented struts extending in a direction opposite the first end; heat-setting the expandable frame to define an expanded configuration of the expandable frame; sliding a constrainment member over the plurality of longitudinally-oriented struts, the constrainment member being formed using additive manufacturing technology; fixedly securing the constrainment member to the plurality of longitudinally-oriented struts to define a second hub of the expandable frame; and cutting the plurality of longitudinally-oriented struts adjacent the constrainment member and opposite the first end relative to the constrainment member.

11 Claims, 9 Drawing Sheets

(51) Int. Cl.
*B33Y 10/00* (2015.01)
*A61B 17/00* (2006.01)
(52) U.S. Cl.
CPC ............ *A61B 2017/00526* (2013.01); *A61B 2017/12054* (2013.01); *B33Y 10/00* (2014.12)
(58) Field of Classification Search
CPC ... B33Y 80/00; B33Y 10/00; A61B 17/12172; A61B 17/12109; A61B 2017/00526; A61B 2017/12054; Y02P 10/25
See application file for complete search history.

(56) References Cited

U.S. PATENT DOCUMENTS

| | | |
|---|---|---|
| 5,238,004 A | 8/1993 | Sahatjian et al. |
| 5,250,071 A | 10/1993 | Palermo |
| 5,282,478 A | 2/1994 | Fleischhaker, Jr. et al. |
| 5,304,195 A | 4/1994 | Twyford, Jr. et al. |
| 5,312,415 A | 5/1994 | Palermo |
| 5,546,958 A | 8/1996 | Thorud et al. |
| 5,772,609 A | 6/1998 | Nguyen et al. |
| 6,139,510 A | 10/2000 | Palermo |
| RE37,117 E | 3/2001 | Palermo |
| 6,277,125 B1 | 8/2001 | Barry et al. |
| 6,491,646 B1 | 12/2002 | Blackledge |
| 6,508,803 B1 | 1/2003 | Horikawa et al. |
| 7,044,134 B2 | 5/2006 | Khairkhahan et al. |
| 7,708,755 B2 | 5/2010 | Davis et al. |
| 7,815,661 B2 | 10/2010 | Mirizzi et al. |
| 7,896,899 B2 | 3/2011 | Patterson et al. |
| 8,142,456 B2 | 3/2012 | Rosqueta |
| 8,236,042 B2 | 8/2012 | Berez et al. |
| 8,333,786 B2 | 12/2012 | Mirizzi et al. |
| 8,333,796 B2 | 12/2012 | Tompkins et al. |
| 8,641,777 B2 | 2/2014 | Strauss et al. |
| 8,696,701 B2 | 4/2014 | Becking et al. |
| 8,747,597 B2 | 6/2014 | Rosqueta et al. |
| 8,795,313 B2 | 8/2014 | Liang et al. |
| 8,801,746 B1 | 8/2014 | Kreidler et al. |
| 8,911,487 B2 | 12/2014 | Bennett et al. |
| 9,017,350 B2 | 4/2015 | Karabey et al. |
| 9,017,361 B2 | 4/2015 | Karabey et al. |
| 9,060,773 B2 | 6/2015 | Nguyen et al. |
| 9,095,342 B2 | 8/2015 | Becking et al. |
| 9,119,948 B2 | 9/2015 | Lee et al. |
| 9,186,151 B2 | 11/2015 | Tompkins et al. |
| 9,198,670 B2 | 12/2015 | Hewitt et al. |
| 9,301,827 B2 | 4/2016 | Strauss et al. |
| 9,307,999 B2 | 4/2016 | Li et al. |
| 9,468,442 B2 | 10/2016 | Huynh et al. |
| 9,498,226 B2 | 11/2016 | Cage et al. |
| 9,549,740 B2 | 1/2017 | Rees |
| 9,554,805 B2 | 1/2017 | Tompkins et al. |
| 9,693,852 B2 | 7/2017 | Lam et al. |
| 2006/0036281 A1 | 2/2006 | Patterson et al. |
| 2006/0212055 A1 | 9/2006 | Karabey et al. |
| 2006/0229669 A1 | 10/2006 | Mirizzi et al. |
| 2006/0282159 A1 | 12/2006 | Taheri |
| 2007/0135826 A1 | 6/2007 | Zaver et al. |
| 2007/0173885 A1* | 7/2007 | Cartier .................. A61F 2/012 606/200 |
| 2007/0270903 A1 | 11/2007 | Davis et al. |
| 2007/0282373 A1 | 12/2007 | Ashby et al. |
| 2007/0293928 A1 | 12/2007 | Tomlin |
| 2008/0109059 A1 | 5/2008 | Gordon et al. |
| 2008/0119891 A1 | 5/2008 | Miles et al. |
| 2008/0300616 A1 | 12/2008 | Que et al. |
| 2009/0043331 A1 | 2/2009 | Buiser et al. |
| 2009/0062838 A1 | 3/2009 | Brumleve et al. |
| 2009/0062845 A1 | 3/2009 | Tekulve |
| 2009/0163934 A1 | 6/2009 | Raschdorf, Jr. et al. |
| 2009/0177261 A1 | 7/2009 | Teoh et al. |
| 2009/0270978 A1 | 10/2009 | Virkler et al. |
| 2009/0287291 A1 | 11/2009 | Becking et al. |
| 2009/0287294 A1 | 11/2009 | Rosqueta et al. |
| 2010/0106178 A1 | 4/2010 | Obermiller et al. |
| 2010/0121350 A1 | 5/2010 | Mirigian |
| 2010/0174269 A1 | 7/2010 | Tompkins et al. |
| 2011/0166588 A1 | 7/2011 | Connor et al. |
| 2011/0184454 A1 | 7/2011 | Barry et al. |
| 2011/0202085 A1 | 8/2011 | Loganathan et al. |
| 2011/0238147 A1 | 9/2011 | Bennett et al. |
| 2011/0265943 A1 | 11/2011 | Rosqueta et al. |
| 2011/0319926 A1 | 12/2011 | Becking et al. |
| 2012/0046687 A1 | 2/2012 | Trommeter et al. |
| 2012/0203322 A1 | 8/2012 | Eells |
| 2012/0245675 A1* | 9/2012 | Molaei .............. A61B 17/12118 623/1.16 |
| 2012/0283812 A1 | 11/2012 | Lagodzki |
| 2012/0316598 A1 | 12/2012 | Becking et al. |
| 2012/0330341 A1 | 12/2012 | Becking et al. |
| 2012/0330347 A1 | 12/2012 | Becking et al. |
| 2012/0330348 A1 | 12/2012 | Strauss et al. |
| 2013/0066360 A1 | 3/2013 | Becking et al. |
| 2013/0072961 A1 | 3/2013 | Cage et al. |
| 2013/0085520 A1 | 4/2013 | Liang et al. |
| 2013/0085522 A1 | 4/2013 | Becking et al. |
| 2013/0152941 A1 | 6/2013 | Nguyen et al. |
| 2013/0253572 A1 | 9/2013 | Molaei et al. |
| 2013/0261730 A1 | 10/2013 | Bose et al. |
| 2013/0296917 A1 | 11/2013 | Rees |
| 2013/0331882 A1 | 12/2013 | Tompkins et al. |
| 2014/0018841 A1 | 1/2014 | Peiffer et al. |
| 2014/0058434 A1 | 2/2014 | Jones et al. |
| 2014/0058435 A1 | 2/2014 | Jones et al. |
| 2014/0128907 A1 | 5/2014 | Hui et al. |
| 2014/0135810 A1 | 5/2014 | Divino et al. |
| 2014/0135811 A1 | 5/2014 | Divino et al. |
| 2014/0135812 A1 | 5/2014 | Divino et al. |
| 2014/0148843 A1 | 5/2014 | Strauss et al. |
| 2014/0172001 A1 | 6/2014 | Becking et al. |
| 2014/0236127 A1 | 8/2014 | Lee et al. |
| 2014/0358175 A1 | 12/2014 | Tompkins et al. |
| 2015/0005807 A1 | 1/2015 | Lagodzki et al. |
| 2015/0073524 A1 | 3/2015 | Bennett et al. |
| 2015/0112378 A1 | 4/2015 | Torp |
| 2015/0157332 A1 | 6/2015 | Obermiller et al. |
| 2015/0196304 A1 | 7/2015 | Rabkin et al. |
| 2015/0230802 A1 | 8/2015 | Lagodzki et al. |
| 2015/0257763 A1 | 9/2015 | Blum et al. |
| 2015/0272589 A1 | 10/2015 | Lorenzo |
| 2015/0297240 A1 | 10/2015 | Divino et al. |
| 2015/0327868 A1 | 11/2015 | Islak et al. |
| 2015/0335333 A1 | 11/2015 | Jones et al. |
| 2015/0342611 A1 | 12/2015 | Leopold et al. |
| 2015/0343181 A1 | 12/2015 | Bradway et al. |
| 2016/0008003 A1 | 1/2016 | Kleshinski et al. |
| 2016/0022445 A1 | 1/2016 | Ruvalcaba et al. |
| 2016/0030052 A1 | 2/2016 | Cragg et al. |
| 2016/0166257 A1 | 6/2016 | Allen et al. |
| 2016/0192942 A1 | 7/2016 | Strauss et al. |
| 2016/0228123 A1 | 8/2016 | Anderson et al. |
| 2016/0228124 A1 | 8/2016 | Trommeter et al. |
| 2016/0228128 A1 | 8/2016 | Connolly |
| 2016/0317274 A1 | 11/2016 | Liu et al. |
| 2017/0224355 A1 | 8/2017 | Bowman et al. |

FOREIGN PATENT DOCUMENTS

| | | |
|---|---|---|
| EP | 3085310 A1 | 10/2016 |
| JP | 2016537134 A | 12/2016 |
| WO | 0232496 A1 | 4/2002 |
| WO | 2007047111 A1 | 4/2007 |
| WO | 2007070797 A2 | 6/2007 |
| WO | 2010030993 A1 | 3/2010 |
| WO | 2010098804 A1 | 9/2010 |

(56) References Cited

FOREIGN PATENT DOCUMENTS

WO   2014145012 A1   9/2014
WO   2014145005 A3   4/2015

OTHER PUBLICATIONS

International Search Report and Written Opinion dated Feb. 28, 2018 for International Application No. PCT/US2017/061779.
International Search Report and Written Opinion dated Jul. 13, 2018 for International Application No. PCT/US2018/028240.
International Search Report and Written Opinion dated Dec. 5, 2018 for International Application No. PCT/US2018/000148.

* cited by examiner

METHOD OF MAKING A VASCULAR OCCLUSION DEVICE

CROSS-REFERENCE TO RELATED APPLICATIONS

This application claims the benefit of priority under 35 U.S.C. § 119 to U.S. Provisional Application Ser. No. 62/625,035, filed Feb. 1, 2018, the entirety of which is incorporated herein by reference.

TECHNICAL FIELD

The present disclosure pertains to medical devices and methods for manufacturing and/or using occlusive medical devices. More particularly, the present disclosure pertains to methods of manufacturing a vascular occlusion device.

BACKGROUND

A wide variety of intracorporeal medical devices have been developed for medical is use, for example, surgical and/or intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. There is an ongoing need to provide alternative medical devices as well as alternative methods for manufacturing and/or using medical devices.

SUMMARY

In a first aspect, a method of making a vascular occlusion device may comprise:

cutting a tubular member to form an expandable frame in an as-cut configuration, the expandable frame including: a first hub integrally formed with the expandable frame adjacent a first end of the expandable frame, and a plurality of longitudinally-oriented struts extending in a direction opposite the first end;

heat-setting the expandable frame to define an expanded configuration of the expandable frame;

sliding a constrainment member over the plurality of longitudinally-oriented struts, the constrainment member being formed using additive manufacturing technology;

fixedly securing the constrainment member to the plurality of longitudinally-oriented struts to define a second hub of the expandable frame; and cutting the plurality of longitudinally-oriented struts adjacent the constrainment member and opposite the first end relative to the constrainment member.

In addition or alternatively, and in a second aspect, the method may further comprise inserting a centering rod between the plurality of longitudinally-oriented struts prior to sliding the constrainment member over the plurality of longitudinally-oriented struts, wherein the sliding step further includes sliding the constrainment member over the centering rod.

In addition or alternatively, and in a third aspect, the fixedly securing step includes fixedly securing the constrainment member to the centering rod. The cutting step includes cutting the centering rod adjacent the constrainment member.

In addition or alternatively, and in a fourth aspect, the method may further comprise inserting a centering rod through the constrainment member between the plurality of longitudinally-oriented struts after sliding the constrainment member over the plurality of longitudinally-oriented struts.

In addition or alternatively, and in a fifth aspect, the constrainment member includes a plurality of internal teeth open to a central passage.

In addition or alternatively, and in a sixth aspect, the plurality of internal teeth defines a tooth length, the tooth length being about 75% or less of a length of the constrainment member.

In addition or alternatively, and in a seventh aspect, the tooth length is about 50% or less of the length of the constrainment member.

In addition or alternatively, and in an eighth aspect, a vascular occlusion device may comprise an expandable frame cut from a tubular member, the expandable frame including: a first hub integrally formed with the expandable frame adjacent a first end of the expandable frame, and a plurality of longitudinally-oriented struts extending in a direction opposite the first end; and a constrainment member formed using additive manufacturing technology, the constrainment member being fixedly secured to the plurality of longitudinally-oriented struts to define a second hub adjacent a second end of the expandable frame.

In addition or alternatively, and in a ninth aspect, the constrainment member includes a plurality of internal teeth open to a central passage.

In addition or alternatively, and in a tenth aspect, the plurality of internal teeth defines a tooth length, the tooth length being about 75% or less of a length of the constrainment member.

In addition or alternatively, and in an eleventh aspect, the tooth length is about 50% or less of the length of the constrainment member.

In addition or alternatively, and in a twelfth aspect, each adjacent pair of internal teeth defines one longitudinally-oriented slot configured to receive one of the plurality of longitudinally-oriented struts.

In addition or alternatively, and in a thirteenth aspect, each longitudinally-oriented strut is received in a different longitudinally-oriented slot.

In addition or alternatively, and in a fourteenth aspect, the vascular occlusion device may further comprise a centering rod disposed within the central passage.

In addition or alternatively, and in a fifteenth aspect, the centering rod urges the plurality of longitudinally-oriented struts into longitudinally-oriented slots defined by the plurality of teeth.

In addition or alternatively, and in a sixteenth aspect, a vascular occlusion device may comprise an expandable frame laser cut from a tubular member, the expandable frame including: a proximal hub integrally formed with the expandable frame adjacent a proximal end of the expandable frame, a plurality of closed cells forming a series of adjacent rows of cells along a length of the expandable frame, the proximal hub having a fixed outer diameter less than an outer diameter of the series of adjacent rows of cells in an expanded configuration, and a plurality of longitudinally-oriented struts extending distally away from the plurality of closed cells; and a constrainment member having a plurality of internal teeth, the plurality of internal teeth extending along less than a full length of the constrainment member. The constrainment member may be fixedly attached with an adhesive substance to the plurality of longitudinally-oriented struts to define a distal hub adjacent a distal end of the expandable frame.

In addition or alternatively, and in a seventeenth aspect, the constrainment member has a fixed outer diameter less than the outer diameter of the series of adjacent rows of cells in the expanded configuration.

In addition or alternatively, and in an eighteenth aspect, the expandable frame is biased toward the expanded configuration.

In addition or alternatively, and in a nineteenth aspect, the expandable frame includes a shape memory material.

In addition or alternatively, and in a twentieth aspect, the vascular occlusion device may further comprise a radiopaque centering rod fixedly attached to the constrainment member and configured to displace the plurality of longitudinally-oriented struts into slots formed by the plurality of internal teeth.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean a greatest measurement of a stated or identified dimension, unless specifically referred to as a minimum extent. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage. However, where referred to as a "minimum extent", the "extent" shall refer to a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact and/or are affected by the cardiovascular system are prevalent throughout the world. For example, some forms of arterial venous malformations (AVMs) may "feed" off of normal blood flow through the vascular system. Without being bound by theory, it is believed that it may be possible to treat, at least partially, arterial venous malformations and/or other diseases or conditions by starving them of normal, oxygen and/or nutrient-rich blood flow, thereby limiting their ability to grow and/or spread. Other examples of diseases or conditions that may benefit from vascular occlusion include, but are not limited to, bleeds, aneurysms, venous insufficiency, shutting off blood flow prior to organ resection, or preventing embolic bead reflux into branch vessels in the liver. Disclosed herein are medical devices that may be used within a portion of the cardiovascular system in order to treat and/or repair some arterial venous malformations and/or other diseases or conditions, and methods of making such devices. The devices and methods disclosed herein may also provide a number of additional desirable features and benefits as described in more detail below.

Figure 1:
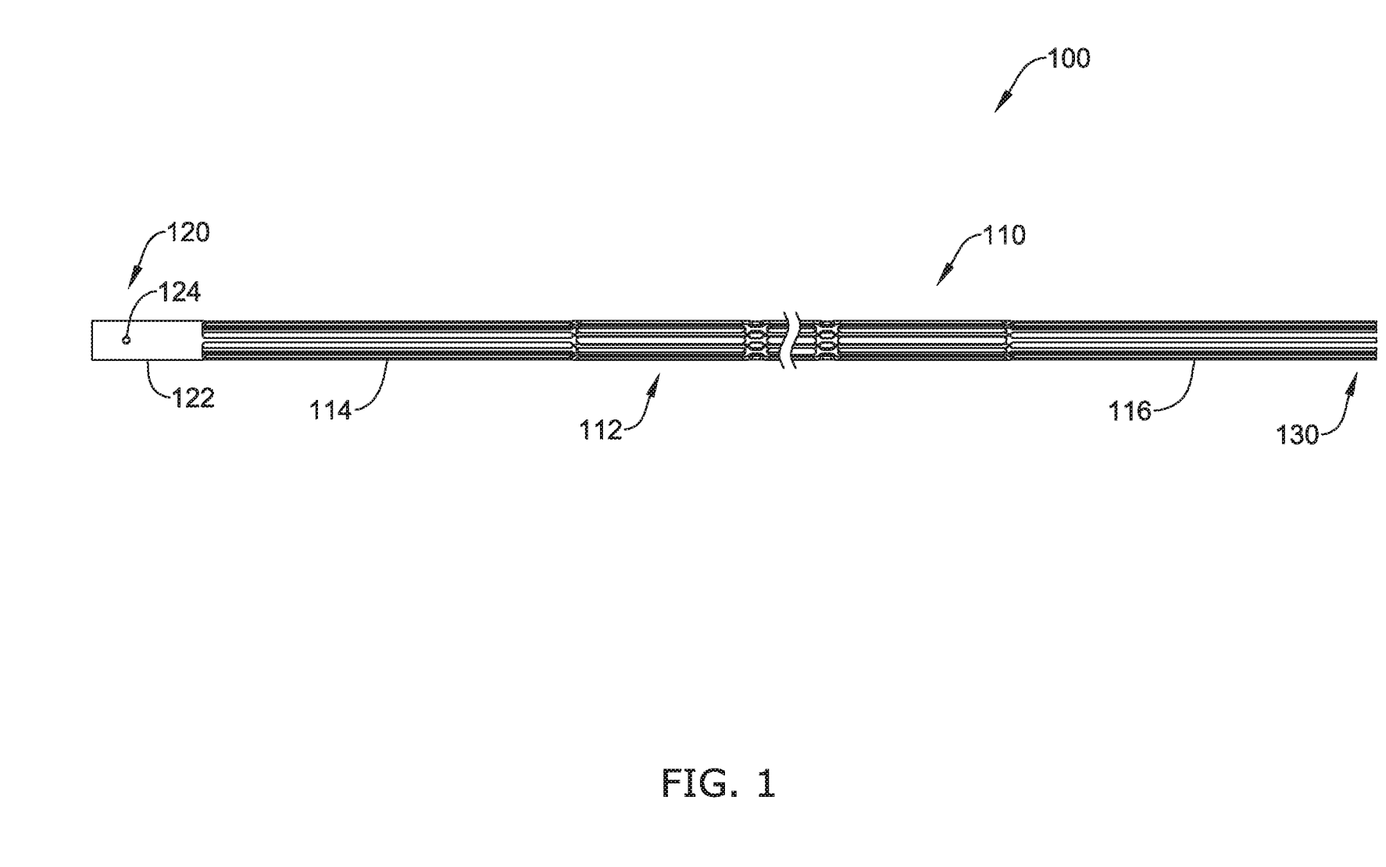
FIGS. 1-3 illustrate aspects of a method of making the example vascular occlusion device.
Figure 2:
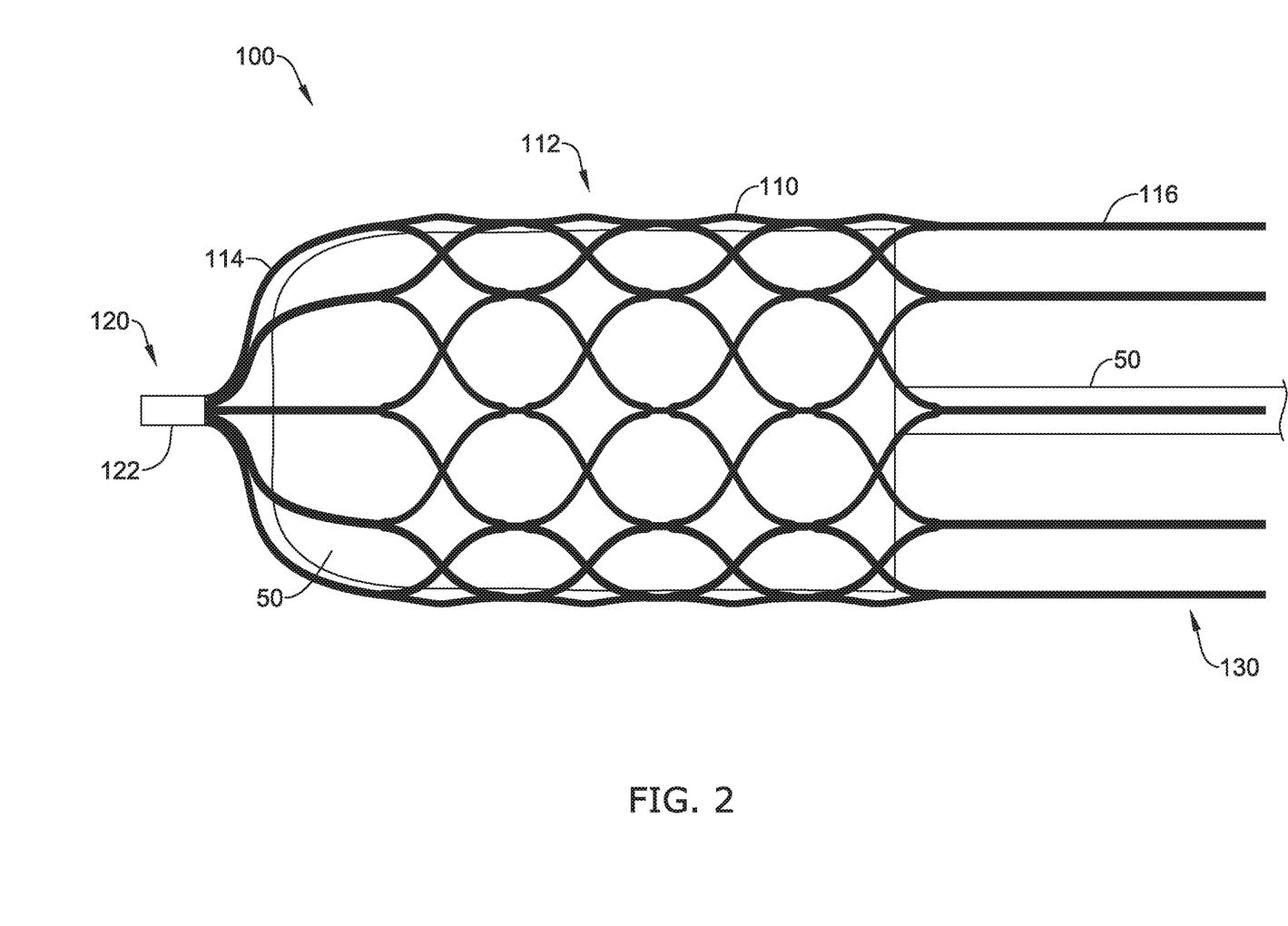
Figure 3:
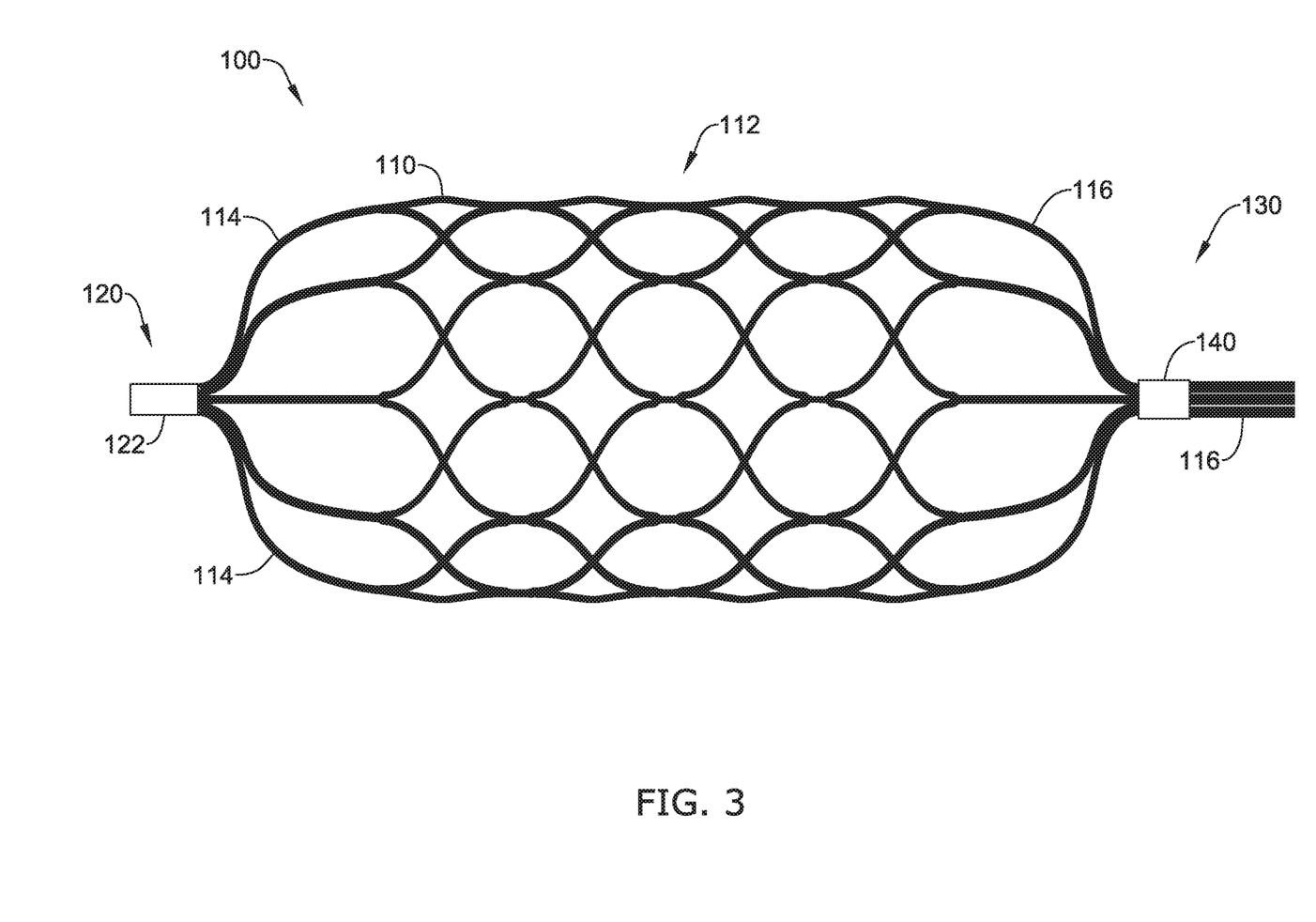

FIG. 1-3 illustrate aspects of a method of making an example vascular occlusion device 100. The vascular occlusion device 100 may include an expandable frame 110 having a first end 120 and a second end 130 opposite the first end 120. The expandable frame 110 may include a body 112 formed from a plurality of interconnected struts and/or a lattice support structure. For example, in some embodiments, the body 112 of the expandable frame 110 may have the form and/or appearance of an expandable stent. In some embodiments, the expandable frame 110 and/or the body 112 of the expandable frame 110 may include a plurality of closed cells forming a series of adjacent rows of cells along a length of the expandable frame 110 and/or the body 112 of the expandable frame 110.

In some embodiments, the method may include cutting a tubular member, a catheter, a hypotube, or other similar tubular structure to form the expandable frame 110 in an as-cut configuration, shown in FIG. 1. In some embodiments, the expandable frame 110 may be formed and/or cut from a flat sheet of material that is subsequently rolled to form a tubular member or tubular structure and welded, bonded, or otherwise joined along a seam and/or a joint formed by edges of the flat sheet of material brought together. In some embodiments, the expandable frame 110 may be laser cut from the tubular member, the catheter, the hypotube, or other similar tubular structure and/or the flat sheet of material. The as-cut configuration of the expandable frame 110 may also generally correspond to and/or correlate to a collapsed configuration and/or a delivery configuration.

The expandable frame 110 may be configured to shift from a collapsed delivery configuration to an expanded configuration upon delivery to a treatment site. In the expanded configuration, the body 112 of the expandable frame 110 and/or the plurality of closed cells forming the series of adjacent rows of cells may be "open" or enlarged compared to the as-cut configuration. In the expanded configuration, the body 112 of the expandable frame 110 and/or the plurality of closed cells forming the series of adjacent rows of cells may define an outer diameter and/or outer extent greater than the outer diameter or outer extent of the body 112 of the expandable frame 110 and/or the plurality of closed cells forming the series of adjacent rows of cells in the as-cut configuration.

The vascular occlusion device 100 and/or the expandable frame 110 may include a first hub 122 integrally formed and/or unitary with the body 112 of the expandable frame 110 adjacent the first end 120 of the expandable frame 110. The expandable frame 110 may include a first plurality of longitudinally-oriented struts 114 extending away from and/or proximally from the body 112 of the expandable frame 110 and/or the plurality of closed cells forming the series of adjacent rows of cells toward and/or to the first hub 122. In some embodiments, the first end 120 may be a proximal end of expandable frame 110, and the second end 130 may be a distal end of the expandable frame 110. In such embodiments, the first hub 122 may be interchangeably referred to as a proximal hub. In some embodiments, the second plurality of longitudinally-oriented struts 116 may extend in a proximal direction from the body 112 of the expandable frame 110 and/or the plurality of closed cells forming the series of adjacent rows of cells In some embodiments, the first plurality of longitudinally-oriented struts 114 may be integrally formed with the body 112 of the expandable frame 110 and the first hub 122. In some embodiments, the first hub 122 (e.g., the proximal hub, etc.) may optionally include an aperture 124 extending through a wall of the first hub 122 (e.g., the proximal hub, etc.). The aperture 124 may permit and/or facilitate releasable attachment of the vascular occlusion device 100 and/or the first hub 122 (e.g., the proximal hub, etc.) to an intravascular delivery device. The first hub 122 (e.g., the proximal hub, etc.) may have a generally fixed outer diameter and/or outer extent that does not expand and/or change with expansion of the body 112 of the expandable frame 110. The first hub 122 (e.g., the proximal hub, etc.) may be circumferentially continuous and/or may be circumferentially closed around a central longitudinal axis of the vascular occlusion device 100 and/or the expandable frame 110.

The vascular occlusion device 100 and/or the expandable frame 110 may include a second plurality of longitudinally-oriented struts 116 extending away from the body 112 of the expandable frame 110 and/or the plurality of closed cells forming the series of adjacent rows of cells in a direction opposite the first end 120 of the expandable frame 110 and/or the first hub 122 (e.g., the proximal hub, etc.). For example, the second plurality of longitudinally-oriented struts 116 may extend in a distal direction from the body 112 of the expandable frame 110 and/or the plurality of closed cells forming the series of adjacent rows of cells. Each of the second plurality of longitudinally-oriented struts 116 may extend to a free end. Some suitable but non-limiting materials for the expandable frame 110, the body 112, the first plurality of longitudinally-oriented struts 114, and the second plurality of longitudinally-oriented struts 116, for example metallic materials, polymer materials, composite materials, shape memory materials, etc., are described below.

As seen in FIG. 2, the method may include inserting a mandrel 50 between the free ends of the second plurality of longitudinally-oriented struts 116 and/or into the expandable frame 110 and/or the body 112 of the expandable frame 110 to expand the expandable frame 110 and/or the body 112 of the expandable frame 110 toward and/or into the expanded configuration. The expandable frame 110, the body 112 of the expandable frame 110, and/or the first plurality of longitudinally-oriented struts 114 may generally take the shape of the mandrel 50 proximate the first end 120 of the expandable frame 110, although other configurations are also contemplated. Some suitable but non-limiting materials for the mandrel 50, for example metallic materials, polymer materials, composite materials, etc., are zo described below.

The method may include heat-setting the expandable frame 110, the body 112 of the expandable frame 110, the plurality of closed cells forming the series of adjacent rows of cells, and/or the first plurality of longitudinally-oriented struts 114 to define the expanded configuration of the expandable frame 110 and/or the body 112 of the expandable frame 110. In some embodiments, the method may include heat-setting the expandable frame 110, the body 112 of the expandable frame 110, the plurality of closed cells forming the series of adjacent rows of cells, and/or the first plurality of longitudinally-oriented struts 114 to define the expanded configuration of the expandable frame 110 and/or the body 112 of the expandable frame 110 with the mandrel 50 in place and/or disposed within the expandable frame 110.

The first hub 122 (e.g., the proximal hub) may have a fixed outer diameter and/or outer extent less than the outer diameter or outer extent of the body 112 of the expandable frame 110 and/or the plurality of closed cells forming the series of adjacent rows of cells in the expanded configuration. The expandable frame 110, the body 112 of the expandable frame 110, the plurality of closed cells forming the series of adjacent rows of cells, and/or the first plurality of longitudinally-oriented struts 114 may include and/or be formed from a shape memory material. In at least some embodiments, the expandable frame 110, the body 112 of the expandable frame 110, the plurality of closed cells forming the series of adjacent rows of cells, and/or the first plurality of longitudinally-oriented struts 114 may be biased towards the expanded configuration after heat-setting. In some embodiments, the expandable frame 110, the body 112 of the expandable frame 110, the plurality of closed cells forming the series of adjacent rows of cells, and/or the first plurality of longitudinally-oriented struts 114 may be self-biased towards the expanded configuration after heat-setting.

The method may include removing the expandable frame 110 from the mandrel 50 or removing the mandrel 50 from the expandable frame 110. In some embodiments, removing the expandable frame 110 from the mandrel 50 or removing the mandrel 50 from the expandable frame 110 may occur after heat-setting the expandable frame 110, the body 112 of the expandable frame 110, the plurality of closed cells forming the series of adjacent rows of cells, and/or the first plurality of longitudinally-oriented struts 114 to define the expanded configuration. The second plurality of longitudinally-oriented struts 116 may be formed, drawn together, and/or bent radially inward toward a central longitudinal axis of the expandable frame 110, wherein the free ends of the second plurality of longitudinally-oriented struts 116 may be aligned generally parallel to the central longitudinal axis of the expandable frame 110. As shown in FIG. 3 for example, the method may include sliding a constrainment member 140 over the second plurality of longitudinally-oriented struts.

Figure 4:
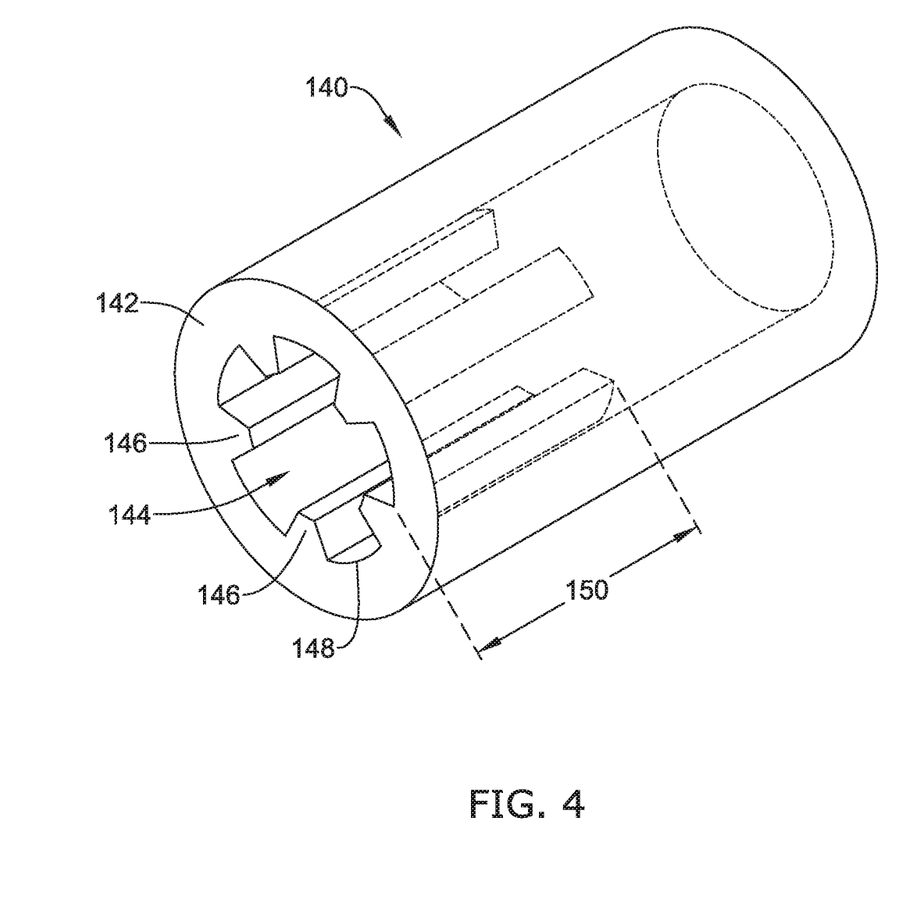
FIGS. 4-5 illustrate an example constrainment member for use with the example vascular occlusion device.
Figure 5:
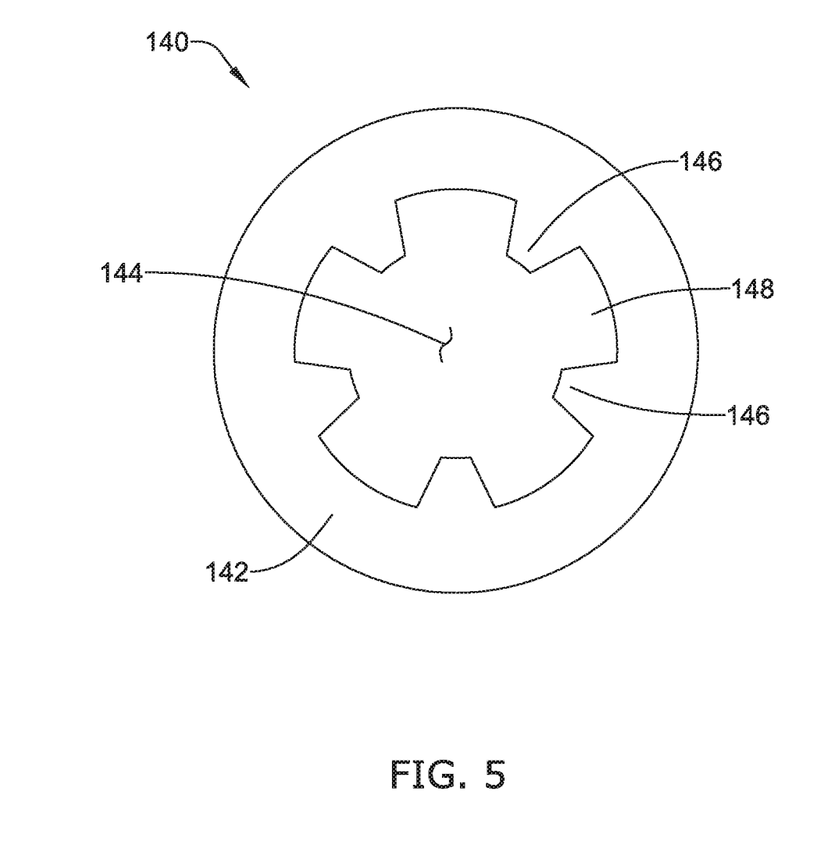

FIGS. 4-5 illustrate an example of the constrainment member 140, which may be formed using additive manufacturing technology. Additive manufacturing technology may be considered to generally refer to processes that add material to form a part, component, or feature (e.g., material deposition, 3D printing, stereolithography, laser sintering, etc.), in contrast to subtractive processes which remove material from a substrate or raw material (e.g., machining, cutting, punching, etc.) and/or non-additive processes (stamping, casting, etc.). Due to the very small size of the components involved in intravascular medical devices (e.g., 0.025 inches maximum outer extent or less), additive manufacturing processes may be more successful at reliably producing internal features of those components. However, it is contemplated that other processes may be used, improved, and/or developed to produce the constrainment member 140.

The constrainment member 140 may be a generally tubular element having a longitudinally-extending wall 142. The constrainment member 140 and/or the longitudinally-extending wall 142 may define a central passage 144 extending through the constrainment member and/or the longitudinally-extending wall 142 along a central longitudinal axis of the constrainment member 140. In at least some embodiments, the longitudinally-extending wall 142 may completely encircle, surround, and/or circumferentially enclose the central passage 144 and/or the central longitudinal axis of the constrainment member 140. The constrainment member 140 and/or the longitudinally-extending wall 142 may have a fixed outer diameter and/or outer extent less than the outer diameter and/or outer extent of the body 112 of the expandable frame 110 and/or the plurality of closed cells forming the series of adjacent rows of cells in the expanded configuration.

The constrainment member 140 may include a plurality of internal teeth 146 open to and/or extending radially inward toward the central passage 144 from the longitudinally-extending wall 142, the plurality of internal teeth 146 defining a plurality of longitudinally-oriented slots 148. Each adjacent pair of internal teeth 146 may define one longitudinally-oriented slot 148 configured to receive one of the second plurality of longitudinally-oriented struts 116. In some embodiments, each of the second plurality of longitudinally-oriented struts 116 may be received in a different longitudinally-oriented slot 148. The plurality of internal teeth 146 may define a tooth length 150. The tooth length 150 may extend along less than a full or overall length of the constrainment member 140. In some embodiments, the tooth length 150 may be about 75% or less of the overall length of the constrainment member 140. In some embodiments, the tooth length 150 may be about 50% or less of the overall length of the constrainment member 140. Having the plurality of internal teeth 146 extend less than the full or overall length of the constrainment member 140 may provide additional space and/or volume within the constrainment member 140 for an adhesive substance, a bonding agent, a weld, and/or other joining means to fixedly secure the constrainment member 140 to the second plurality of longitudinally-oriented struts 116, as discussed herein. Some suitable but non-limiting materials for the constrainment member 140, for example metallic materials, polymer materials, composite materials, etc., are described below.

Figure 6:
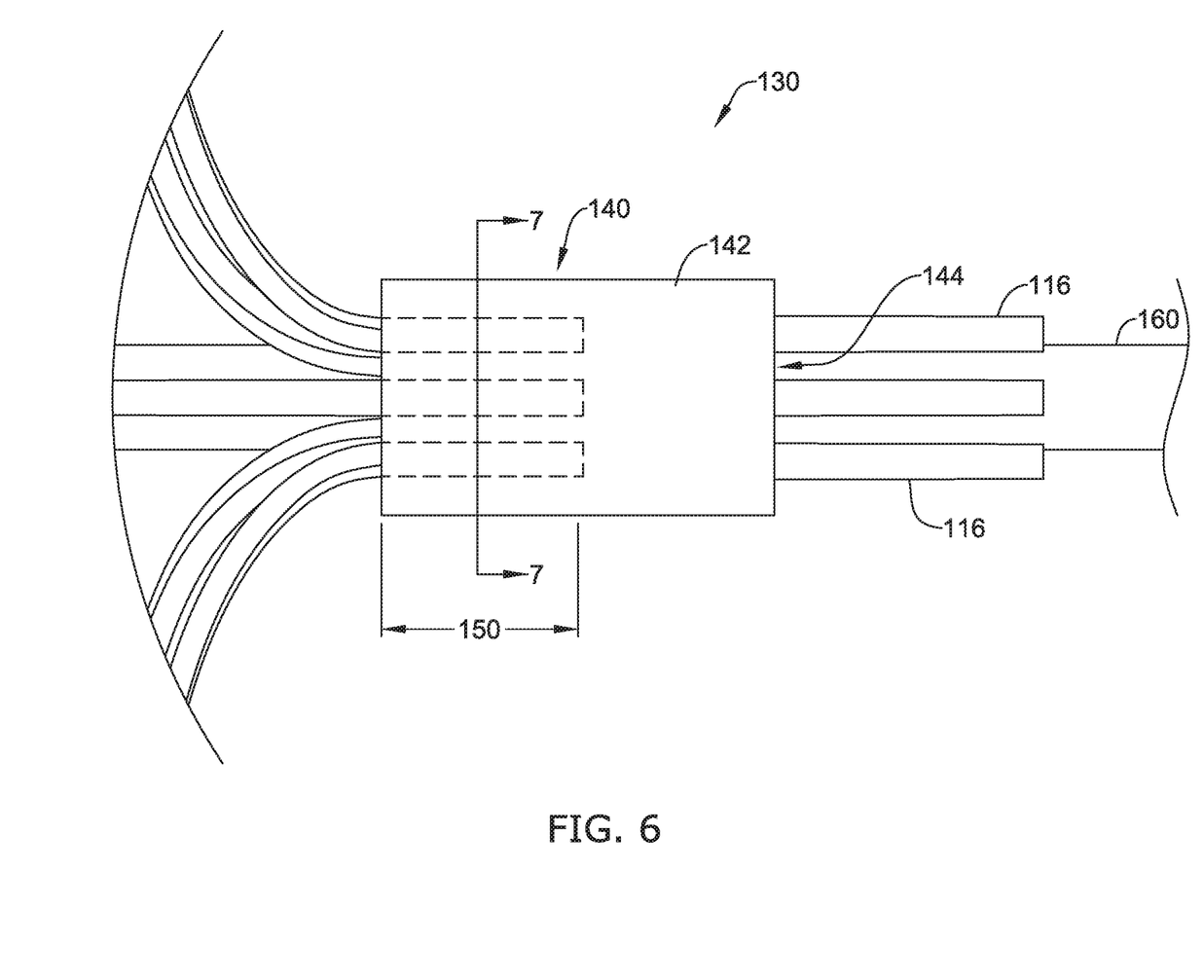
FIG. 6 illustrates aspects of a method of making the example vascular occlusion device.
Figure 7:
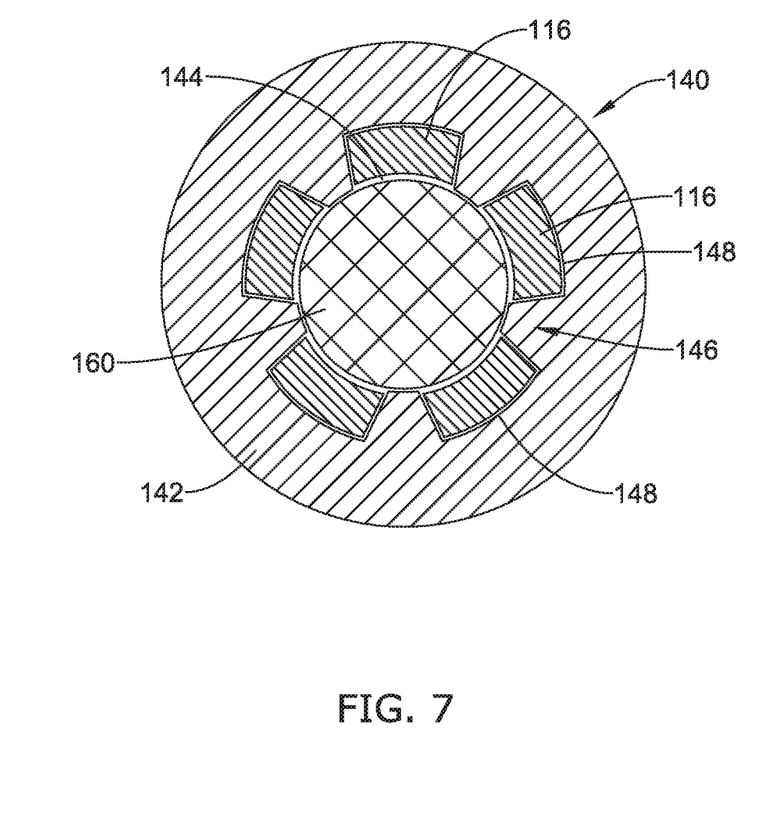
FIG. 7 illustrates a cross-section taken through line 7-7 in FIG. 6.

As illustrated in FIGS. 6-7, the method may include inserting a centering rod 160 between the free ends of the second plurality of longitudinally-oriented struts 116 and/or through the central passage 144 of the constrainment member 140. The centering rod 160 may be a solid shaft, a tubular shaft, and/or a combination thereof.

In some embodiments, the method may include inserting the centering rod 160 between the second plurality of longitudinally-oriented struts 116 prior to sliding the constrainment member 140 over the second plurality of longitudinally-oriented struts 116. In such embodiments, the method may further include sliding the constrainment member 140 over the centering rod 160. In some embodiments, the method may include inserting the centering rod 160 through the constrainment member 140 between the second plurality of longitudinally-oriented struts 116 after sliding the constrainment member 140 over the second plurality of longitudinally-oriented struts 116.

As seen in FIG. 7 for example, the centering rod 160 may be disposed within the central passage 144 of the constrainment member 140. The centering rod 160 may substantially fill and/or occupy a portion of the central passage 144 defined by radially-inwardmost tips of the plurality of internal teeth 146 along and/or coaxial with a central longitudinal axis of the constrainment member 140. In at least some embodiments, the centering rod 160 may urge and/or displace the second plurality of longitudinally-oriented struts 116 into the plurality of longitudinally-oriented slots 148 defined by the plurality of internal teeth 146 of the constrainment member 140. In some embodiments, the centering rod 160 may be formed from and/or may include a radiopaque material. In some embodiments, the centering rod 160 may include an enlarged end configured to prevent translation of the end of the centering rod 160 back through the second plurality of longitudinally-oriented struts 116 and/or the constrainment member 140 after the constrainment member 140 is slid over the second plurality of longitudinally-oriented struts 116 and the centering rod 160. Some suitable but non-limiting materials for the centering rod 160, for example metallic materials, polymer materials, composite materials, etc., are described below.

The method may include fixedly securing the constrainment member 140 to the second plurality of longitudinally-oriented struts 116 to define a second hub 132 (e.g., a distal hub) of the expandable frame 110 adjacent the second end 130 (e.g., the distal end) of the expandable frame 110. The constrainment member 140 may be fixedly secured and/or attached with an adhesive substance, a bonding agent, a weld, or another suitable attachment means to the second plurality of longitudinally-oriented struts 116. In some embodiments, the method and/or the fixedly securing step may include fixedly securing the constrainment member 140 to the centering rod 160. In some embodiments, the constrainment member 140, the centering rod 160, and/or the second plurality of longitudinally-oriented struts 116 may be formed from dissimilar materials. As such, welding may be made difficult, thereby supporting and/or necessitating the use of an adhesive substance and/or a bonding agent in place of a weld.

Figure 8:
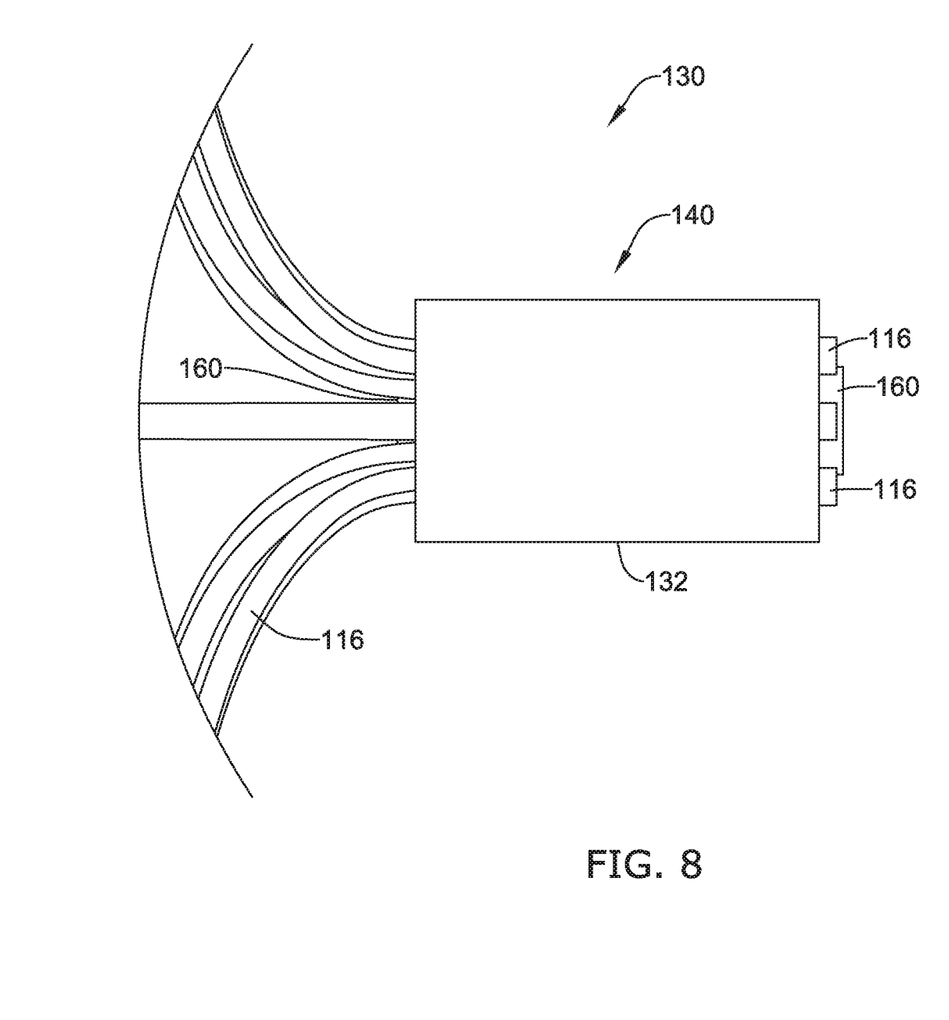
FIGS. 8-9 illustrate aspects of a method of making the example vascular occlusion device.

The method may further include cutting the second plurality of longitudinally-oriented struts 116 adjacent the constrainment member 140 and/or the second hub 132 (e.g., is the distal hub) opposite the first end 120 and/or the first hub 122 (e.g., the proximal hub) relative to the constrainment member 140. For example, the second plurality of longitudinally-oriented struts 116 may be cut and/or trimmed distal of and proximate the second hub 132 (e.g., the distal hub), as shown in FIG. 8. Various methods and/or means of cutting the second plurality of longitudinally-oriented struts 116 may be utilized—including, but not limited to, laser cutting, machining, chemical dissolution, mechanical cutting, etc. In some embodiments, cutting the second plurality of longitudinally-oriented struts 116 may include cutting the centering rod 160 adjacent the constrainment member 140. In some embodiments, the centering rod 160 may be cut both proximal and distal of the constrainment member 140. In some embodiments, the centering rod 160 may be translated distally until the end of the centering rod 160 disposed proximal of the constrainment member 140 is disposed proximate a proximal edge of the constrainment member 140, and the centering rod 160 may then be cut distal of the constrainment member 140 proximate a distal end of the constrainment member 140.

In some embodiments, cutting the second plurality of longitudinally-oriented struts 116 and/or the centering rod 160 may occur before fixedly securing the second plurality of longitudinally-oriented struts 116 and/or the centering rod 160 to the constrainment member 140. In some embodiments, cutting the second plurality of longitudinally-oriented struts 116 and/or the centering rod 160 adjacent the constrainment member 140 may occur after fixedly securing the second plurality of longitudinally-oriented struts 116 and/or the centering rod 160 to the constrainment member 140. In some embodiments, varying combinations of these temporal arrangements are also contemplated.

Figure 9:
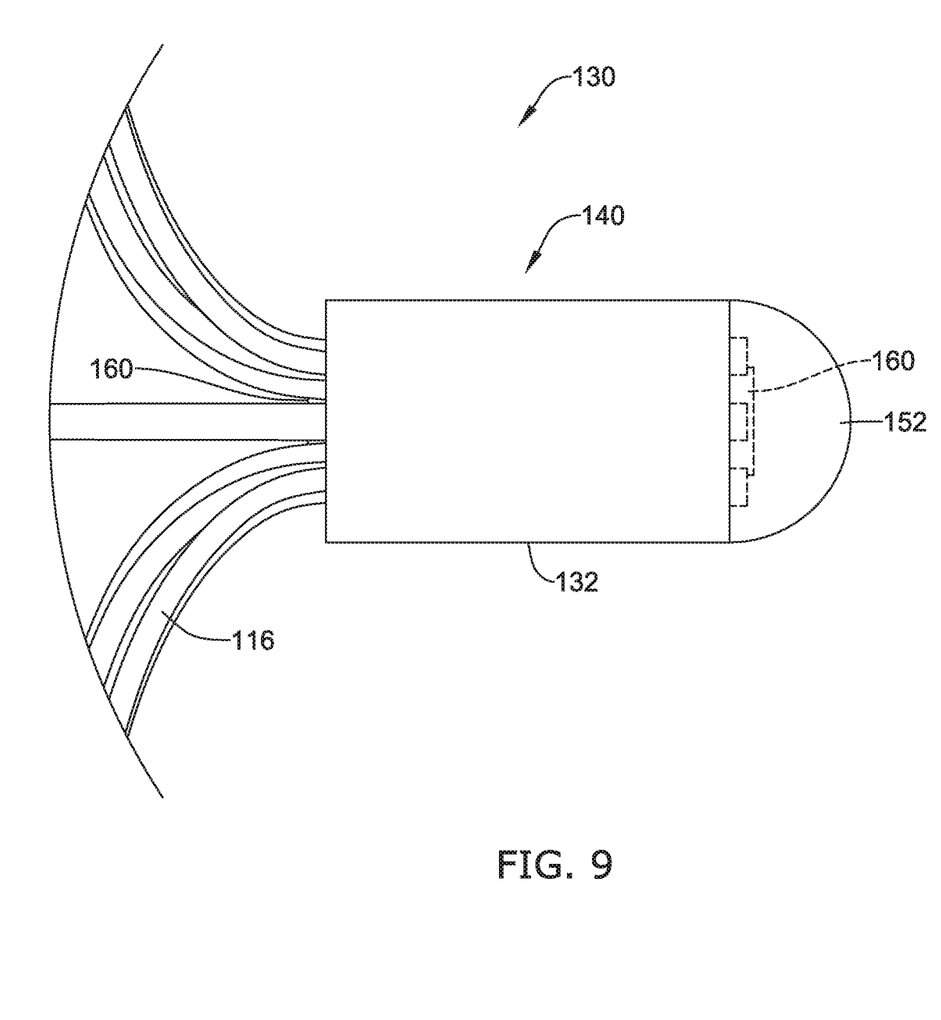

In some embodiments, the method may include forming an atraumatic tip 152 on the constrainment member 140 after cutting the second plurality of longitudinally-oriented struts 116 and/or the centering rod 160, as seen in FIG. 9. In some embodiments, the atraumatic tip 152 may be an atraumatic distal tip. For example, the atraumatic tip 152 may face distally with respect to the expandable frame 110 and/or may define a distalmost end of the vascular occlusion device 100 and/or the expandable frame 110. In some embodiments, the atraumatic tip 152 may be formed with an adhesive substance, a bonding agent, a weld, or another suitable means. In some embodiments, the adhesive substance, bonding agent, weld, etc. used to form the atraumatic tip 152 may be the same adhesive substance, bonding agent, weld, etc. used to fixedly secure the second plurality of longitudinally-oriented struts 116 and/or the centering rod 160 to the constrainment member 140. In some embodiments, the adhesive substance, bonding agent, weld, etc. used to form the atraumatic tip 152 may be different from the adhesive substance, bonding agent, weld, etc. used to fixedly secure the second plurality of longitudinally-oriented struts 116 and/or the centering rod 160 to the constrainment member 140. In at least some embodiments, the adhesive substance, bonding agent, weld, etc. used to form the atraumatic tip 152 may be compatible with and/or securable directly to the adhesive substance, bonding agent, weld, etc. used to fixedly secure the second plurality of longitudinally-oriented struts 116 and/or the centering rod 160 to the constrainment member 140.

In some embodiments, the vascular occlusion device 100 may optionally include an occlusive membrane formed on and/or attached to at least a portion of the expandable frame 110. In some embodiments, at least a portion of the expandable frame 110 may be embedded within and/or disposed between adjacent layers of the occlusive membrane. In some embodiments, the occlusive membrane may have a closed end and an open end. In some embodiments, the occlusive membrane may have an open first end or proximal end at and/or corresponding to the first hub 122 (e.g., the proximal hub, etc.) of the expandable frame 110, and a closed second end or distal end near and/or corresponding to the second hub 132 (e.g., the distal hub, etc.) of the expandable frame 110. Other configurations are also contemplated. Some suitable but non-limiting materials for the occlusive membrane, for example metallic materials, polymer materials, composite materials, etc., are described below.

The materials that can be used for the various components of the mandrel 50, the vascular occlusion device 100, the expandable frame 110, the constrainment member 140, the centering rod 160, etc. (and/or other systems disclosed herein) and the various elements thereof disclosed herein may include those commonly associated with medical devices. For simplicity purposes, the following discussion makes reference to the mandrel 50, the vascular occlusion device 100, the expandable frame 110, the constrainment member 140, the centering rod 160, etc. However, this is not intended to limit the devices and methods described herein, as the discussion may be applied to other elements, members, components, or devices disclosed herein, such as, but not limited to, the mandrel 50, the vascular occlusion device 100, the expandable frame 110, the constrainment member 140, the centering rod 160, etc. and/or elements or components thereof.

In some embodiments, the mandrel 50, the vascular occlusion device 100, the expandable frame 110, the constrainment member 140, the centering rod 160, etc., and/or components thereof (such as, but not limited to, the body 112, the first plurality of longitudinally-oriented struts 114, the second plurality of longitudinally-oriented struts 116, the first hub 122, the second hub 132, the longitudinally-extending wall 142, the plurality of internal teeth 146, the longitudinally-oriented slots 148, the atraumatic tip 152, etc.), may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-superelastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the vascular occlusion device 100, the expandable frame 110, the constrainment member 140, the centering rod 160, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the vascular occlusion device 100, the expandable frame 110, the constrainment member 140, the centering rod 160, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the vascular occlusion device 100, the expandable frame 110, the constrainment member 140, the centering rod 160, etc. to achieve the same result.

In some embodiments, a degree of Magnetic Resonance Imaging (MM) compatibility is imparted into the vascular occlusion device 100, the expandable frame 110, the constrainment member 140, the centering rod 160, etc. For example, the vascular occlusion device 100, the expandable frame 110, the constrainment member 140, the centering rod 160, etc., and/or components or portions thereof, may be made of a material that does not substantially distort the image and create substantial artifacts (e.g., gaps in the image). Certain ferromagnetic materials, for example, may not be suitable because they may create artifacts in an MM image. The vascular occlusion device 100, the expandable frame 110, the constrainment member 140, the centering rod 160, etc., or portions thereof, may also be made from a material that the Mill machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the mandrel 50, the vascular occlusion device 100, the expandable frame 110, the constrainment member 140, the centering rod 160, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the mandrel 50, the vascular occlusion device 100, the expandable frame 110, the constrainment member 140, the centering rod 160, etc. disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the mandrel 50, the vascular occlusion device 100, the expandable frame 110, the constrainment member 140, the centering rod 160, etc. may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the mandrel 50, the vascular occlusion device 100, the expandable frame 110, the constrainment member 140, the centering rod 160, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A vascular occlusion device, comprising:
an expandable frame cut from a tubular member, the expandable frame including:
a first hub integrally formed with the expandable frame adjacent a first end of the expandable frame, and
a plurality of longitudinally-oriented struts extending in a direction opposite the first end; and
a constrainment member formed using additive manufacturing technology, the constrainment member being fixedly secured to the plurality of longitudinally-oriented struts to define a second hub adjacent a second end of the expandable frame,
wherein the constrainment member includes a plurality of internal teeth open to a central passage,
wherein the plurality of internal teeth defines a tooth length, the tooth length being about 75% or less of a length of the constrainment member.

2. The vascular occlusion device of claim 1, wherein the tooth length is about 50% or less of the length of the constrainment member.

3. The vascular occlusion device of claim 1, wherein each adjacent pair of internal teeth defines one longitudinally-oriented slot configured to receive one of the plurality of longitudinally-oriented struts.

4. The vascular occlusion device of claim 3, wherein each longitudinally-oriented strut is received in a different longitudinally-oriented slot.

5. The vascular occlusion device of claim 1, further comprising a centering rod disposed within the central passage.

6. The vascular occlusion device of claim 5, wherein the centering rod urges the plurality of longitudinally-oriented struts into longitudinally-oriented slots defined by the plurality of internal teeth.

7. A vascular occlusion device, comprising:
an expandable frame laser cut from a tubular member, the expandable frame including:
a proximal hub integrally formed with the expandable frame adjacent a proximal end of the expandable frame,
a plurality of closed cells forming a series of adjacent rows of cells along a length of the expandable frame, the proximal hub having a fixed outer diameter less than an outer diameter of the series of adjacent rows of cells in an expanded configuration and
a plurality of longitudinally-oriented struts extending distally away from the plurality of closed cells; and
a constrainment member having a plurality of internal teeth, the plurality of internal teeth extending along less than a full length of the constrainment member;
wherein the constrainment member is fixedly attached with an adhesive substance to the plurality of longitudinally-oriented struts to define a distal hub adjacent a distal end of the expandable frame,
further comprising a radiopaque centering rod fixedly attached to the constrainment member and configured to displace the plurality of longitudinally-oriented struts into slots formed by the plurality of internal teeth.

8. The vascular occlusion device of claim 7, wherein the constrainment member has a fixed outer diameter less than the outer diameter of the series of adjacent rows of cells in the expanded configuration.

9. The vascular occlusion device of claim 7, wherein the expandable frame is biased toward the expanded configuration.

10. The vascular occlusion device of claim 7, wherein the expandable frame includes a shape memory material.

11. A vascular occlusion device, comprising:
an expandable frame cut from a tubular member, the expandable frame including:
a first hub integrally formed with the expandable frame adjacent a first end of the expandable frame, and
a plurality of longitudinally-oriented struts extending in a direction opposite the first end;
a constrainment member formed using additive manufacturing technology, the constrainment member being fixedly secured to the plurality of longitudinally-oriented struts to define a second hub adjacent a second end of the expandable frame,
wherein the constrainment member includes a plurality of internal teeth open to a central passage; and
a centering rod disposed within the central passage,
wherein the centering rod urges the plurality of longitudinally-oriented struts into longitudinally-oriented slots defined by the plurality of internal teeth.

* * * * *